United States Patent [19]

Shieh et al.

[11] Patent Number: 5,326,701
[45] Date of Patent: Jul. 5, 1994

[54] PROCESS FOR PRODUCING ALPHA-CYCLODEXTRIN USING CYCLOMALTODEXTRIN GLUCANOTRANSFERASE IN PRESENCE OF CYCLOHEXANE

[75] Inventors: Wen J. Shieh; Allan R. Hedges, both of Crown Point, Ind.

[73] Assignee: American Maize Technology Inc., Dimmitt, Tex.

[21] Appl. No.: 28,628

[22] Filed: Mar. 9, 1993

Related U.S. Application Data

[63] Continuation of Ser. No. 772,487, Oct. 7, 1991, abandoned.

[51] Int. Cl.$^5$ .................. C12P 19/18; C12P 19/04; C12N 9/10; C12N 1/20
[52] U.S. Cl. .................... 435/97; 435/101; 435/193; 435/252.31; 435/832; 536/103
[58] Field of Search .......... 435/97, 99, 101, 193, 435/832, 252.31; 536/103

[56] References Cited

U.S. PATENT DOCUMENTS

| | | | |
|---|---|---|---|
| 3,425,910 | 2/1969 | Armbruster et al. | 435/101 |
| 3,541,077 | 11/1970 | Armbruster | 435/101 |
| 3,640,847 | 2/1972 | Armbruster et al. | 435/193 |
| 3,652,398 | 3/1972 | Armbruster et al. | 435/97 |
| 3,826,715 | 7/1974 | Horikoshi et al. | 435/184 |
| 4,028,186 | 6/1977 | Sakai | 435/99 |
| 4,418,144 | 11/1983 | Okada et al. | 435/96 |
| 4,835,105 | 5/1989 | Seres et al. | 435/97 |

*Primary Examiner*—David M. Naff
*Assistant Examiner*—Michael U. Meller
*Attorney, Agent, or Firm*—Lucas & Just

[57] ABSTRACT

A process for producing alpha-cyclodextrin using cyclomaltoextrin glucanotransferase is disclosed. The enzyme is obtained from *Bacillus macerans*. Starch hydrolysate is treated with the enzyme at a temperature of between about 15° C. and about 40° C. wherein the conversion is performed in the presence of cyclohexane and substantially no gamma-cyclodextrin is produced. The resulting alpha-cyclodextrin is then recovered.

10 Claims, No Drawings

PROCESS FOR PRODUCING ALPHA-CYCLODEXTRIN USING CYCLOMALTODEXTRIN GLUCANOTRANSFERASE IN PRESENCE OF CYCLOHEXANE

This is a continuation of application Ser. No. 07/772,487, filed Oct. 7, 1991, now abandoned.

This invention relates to cyclodextrins and, more particularly, to a method for increasing the production of alpha- and beta-cyclodextrin with an amylase called cyclodextrin glucosyl (cyclomaltodextrin glucanotransferase) obtained from *Bacillus macerans*.

Amylases are enzymes which are capable of catalyzing the hydrolysis of the alpha 1,4 linkage in amylose and amylopectin, the two glucose polymers that make up starch. Amylases are produced by a wide variety of plants, bacteria and animals.

Cyclodextrin glucosyl transferase (CGTase), also referred to as cycloamylose glucanotransferase, was first isolated from a bacteria, *Bacillus macerans*, in 1939 by Tilden and Hudson. Since then, CGTase has been obtained from *Bacillus megaterium, Bacillus circulans, Bacillus stearothermohilus, Klebsiella pneumoniae,* and Bacillus species (alkalophilic, see U.S. Pat. No. 3,826,715 issued Jul. 30, 1974). CGTases are known for their ability to form cyclodextrins.

Cyclodextrins, also known as Schardinger dextrins, are composed of anhydroglucose units bound together by alpha 1,4 bonds into a ring or torus. The number of anhydroglucose units in the ring determines the name. Alpha-cyclodextrin has 6 anhydroglucose units, while beta-cyclodextrin has 7 anhydroglucose units and gamma-cyclodextrin has 8 anhydroglucose units. When anhydroglucose units are bound to the ring by bonds other than the alpha 1,4 bonds and do not make up the ring itself, the cyclodextrin is referred to as a branched cyclodextrin. Cyclodextrins have applications in many fields because of their ability to form complexes with other compounds.

Cyclodextrins are conventionally made by the action of CGTase on a starch substrate such as a starch or a starch hydrolysate having a DE between 1 and 10. Typically, the hydrolysis reaction is carried out at the optimum pH and temperature for the enzyme. For CGTase obtained from *B. macerans*, the optimum pH is between 5 and 7 and the optimum temperature is between 50 and 60° C.

It is known that CGTase obtained from *B. macerans* when used as a catalyst will cause the production of alpha-, beta- and gamma-cyclodextrins. Typically, the amount of alpha is about 63% by weight; beta is about 30% by weight; and gamma is about 7% by weight of the total amount of cyclodextrin produced.

It is also known that the addition of certain complexants to the reaction medium will cause the equilibrium of the reaction to be shifted so that predominantly alpha-cyclodextrin or predominantly beta-cyclodextrin is produced. For example, U.S. Pat. No. 3,640,847 issued Feb. 8, 1972 teaches that the presence of 1-decanol at a temperature of about 50° C. and a pH of about 7 causes predominantly alpha-cyclodextrin to be produced while toluene causes predominantly beta-cyclodextrin to be produced. The '847 patent also teaches that cyclohexane produces predominantly beta-cyclodextrin when the starch substrate is a starch hydrolysate and a mixture of alpha- and beta-cyclodextrins when the substrate is a gelatinized starch, see Examples I and V respectively.

It has now been discovered that the equilibrium of a reaction between CGTase obtained from *B. macerans* and a starch substrate can be shifted to produce more cyclodextrin and only alpha- and beta-cyclodextrin with substantially no gamma-cyclodextrin by lowering the temperature at which the reaction occurs and by conducting the reaction in the presence of cyclohexane. Specifically, it has now been discovered that if a starch substrate is treated with a cyclodextrin glucosyl transferase obtained from *B. macerans* at a temperature of about 45° C. and below in the presence of cyclohexane, the amount of cyclodextrin produced is increased compared to the amount of cyclodextrin produced at the optimum temperature for the enzyme, 50–6020 C.

This is both surprising and unexpected because conventional thinking had been that decreasing the temperature at which the reaction takes place would merely cause a decrease in the rate of the hydrolysis reaction and would result in a decrease in the production of all cyclodextrin. To find that the amount of cyclodextrin produced actually increases is unexpected.

It is also surprising that virtually no gamma-cyclodextrin is produced since it is known that *B. macerans* normally produces some gamma-cyclodextrin.

It has also been discovered that alpha-cyclodextrin is produced if the starch substrate is a starch hydrolysate. It is surprising that the presence of cyclohexane during the conversion of a starch hydrolysate to cyclodextrin results in an alpha-cyclodextrin product because heretofore cyclohexane was not thought to promote the production of alpha-cyclodextrin.

It has been found that it is the combination of the lower temperature, the presence of the cyclohexane and the *B. macerans* enzyme which causes the increased cyclodextrin production. Neither the lower temperature nor the cyclohexane alone causes the increased production of cyclodextrin, and the combination of lower temperature and cyclohexane with other CGTase does not cause an increased production of cyclodextrin.

It is not known exactly why the combination of temperature and cyclohexane causes the increase in cyclodextrin production. It has been hypothesized that both the temperature and cyclohexane may have an effect on the structure of the enzyme in solution so as to cause the increase in production of the cyclodextrin. Additionally, it is not understood why there is a shift in the amount of individual alpha- and beta-cyclodextrin produced. From a practical standpoint, there is an overall increase in alpha-cyclodextrin.

Suitable starch substrates include gelatinized starch and starch hydrolysates. The base starch can be from any vegetable source to include corn, wheat, potato, rice, tapioca, and sorghum. Additionally, different varieties of the sources such as waxy corn (high in amylopectin) or high amylose corn (high in amylose) can be used. Preferably, the starch is a waxy corn starch. The starch hydrolysate should have a dextrose equivalent (DE) between about 1 and 10 and preferably about 5. The hydrolysate is made by the action of an acid or enzyme on granular starch. Preferably, the starch hydrolysate is made by the action of an alpha-amylase such as bacterial alpha-amylase on gelatinized granular starch. The preferred starch substrate is a waxy starch hydrolysate obtained from waxy corn starch having a DE of about 5.

Cyclodextrin glucosyl transferase suitable for the present invention is one obtained from *Bacillus macerans*. Cyclodextrin glucosyl transferase from *Bacillus macerans* is commercially available. These enzymes are reported to work best at a temperature of about 60° C. It is surprising that such an enzyme works better for producing alpha-cyclodextrin at a temperature of about 45° C. or less.

In the preferred process according to the present invention, a starch hydrolysate is dissolved in water to form an aqueous solution of starch substrate having a solids content between 5 and 40% by weight. Preferably, the solution has a solids content of about 35% by weight based on the total weight of the solution.

The amount of CGTase used to convert the starch substrate varies depending on the activity of the enzyme which is conventionally measured by the Tilden-Hudson procedure (E.B. Tilden and C. S. Hudson in J. Bacteriol, 43, 527–544, 1942). Preferably, the CGTase contains about 600 to 700 Tilden-Hudson units per milliliter.

The pH of the solution during conversion is generally in the range of about 5 to 8 and preferably about 6.0 to 6.5. Conventional means are used to adjust the pH.

The temperature during conversion is maintained at about 45° C. and below; preferably, about 15 to about 40° C. Good results have been obtained at a temperature between about 20 and about 35° C.

Cyclohexane is present in an amount of about 5 to about 10% by volume of the reaction. Preferably, the cyclohexane is present in an amount of about 5% by volume based on the total volume of the reaction before addition of the cyclohexane. Any source of cyclohexane can be used.

The conversion time is about one to about four days.

After treatment of the starch substrate with cyclodextrin glucosyl transferase, the cyclodextrins are recovered. Preferably, the cyclodextrins are recovered by separating the cyclodextrin precipitate from the acyclic materials in solution. Separation of the cyclic materials from the acyclic materials is done suitably by means of centrifugation or filtration.

After the cyclic material is separated from the acyclic material, the solution of cyclic material is adjusted to about 30% solids and subjected to distillation to drive off the cyclohexane. This leaves a solution of alpha- and beta-cyclodextrins which is separated in a conventional manner.

Preferably, the solution of alpha- and beta cyclodextrins is subjected to a conventional carbon treatment. Crystallization is used to recover most of the beta-cyclodextrin. Carbon treatment and crystallization are performed in a conventional manner.

The remaining solution is then treated with a limited amount of cyclohexane to differentially complex the alpha-cyclodextrin. The complex is separated from solution suitably by means of centrifugation or filtration. Next, the complex of cyclohexane and alpha-cyclodextrin is separated by means of distillation. The alpha-cyclodextrin is then carbon treated and crystallized to obtain a pure alpha-cyclodextrin.

These and other aspects of the present invention may be more fully understood with reference to the following examples.

EXAMPLE I

This example illustrates the temperature dependence of the cyclodextrin glucosyl transferase obtained from *B. macerans* on the production of alpha-cyclodextrin from a starch hydrolysate. Table I below illustrates the results.

TABLE I

| Temp. (°C.) | Total Amount (gr/100 ml) | Alpha (%) | Beta (%) |
|---|---|---|---|
| 20 | 11.69 | 39.8 | 60.2 |
| 30 | 12.75 | 26.7 | 73.3 |
| 40 | 14.42 | 13 | 87 |
| 50 | 8.27 | 23 | 77 |
| 60 | 8.05 | 0 | 100 |

The starch substrate was a waxy corn starch hydrolysate having a DE of 5. In order to prepare the cyclodextrins, a 30% (dry basis) starch hydrolysate solution was prepared. The pH was adjusted to 6.0 ±0.2 and cyclohexane was added to the solution in an amount of 5% of total reaction volume. The solution was dosed with cyclodextrin glucosyl transferase at a level of 800 Tilden-Hudson units per 100 grams of starch solids. The reaction mixture was incubated at the different temperatures mentioned in Table I. The conversions were continued with agitation for 3 days. The cyclodextrins produced were harvested and analyzed by High Pressure Liquid Chromatography (HPLC).

The total amount listed in Table I above is the total weight of cyclodextrin produced in grams. The percents of alpha- and beta-cyclodextrin are also listed. No other measurable cyclodextrins were produced, e.g. no gamma-cyclodextrin was produced. This is true for all the examples herein.

EXAMPLE II

This example illustrates the criticality of CGTase from *B. macerans* as compared to another source of CGTase, *B. subtilus*.

Two separate solutions were prepared in accordance with Example I and were incubated at the temperatures listed in Table II below. The amount of cyclodextrin and the percentages of alpha-, beta-, and gamma-cyclodextrins produced by the conversions are reported in Table II below.

TABLE II

| Temp. (°C.) | Enzyme | Total Amount (gr/100 ml) | Alpha (%) | Beta (%) | Gamma (%) |
|---|---|---|---|---|---|
| 20 | B. macerans | 11.69 | 39.8 | 60.2 | 0 |
| 20 | B. subtilus | 14.40 | 0 | 100 | 0 |
| 50 | B. macerans | 8.27 | 23 | 77 | 0 |
| 50 | B. subtilus | 14.70 | 0 | 100 | 0 |

As can be seen from Table II above, there is no increase in the amount of cyclodextrin produced by lowering the temperature of the reaction when the CGTase is obtained from *B. subtilus*. As noted above, both solutions had cyclohexane present. Thus, the lower temperature and cyclohexane alone do not result in an increase in cyclodextrin production. In fact, the lower temperature results in a lower production of cyclodextrin with the *B. subtilus* enzyme.

EXAMPLE III

This example illustrates the criticality of the presence of the cyclohexane in the solution and that one would normally expect a lower temperature to slow the reaction and produce less product.

Solutions of starch hydrolysates were incubated with *B. macerans* in accordance with Example I at the temperatures listed in Table III below in the absence of cyclohexane.

TABLE III

| Temp. (°C.) | Total Amount (Gr/100 ml) | Alpha(%) | Beta(%) | Gamma(%) |
|---|---|---|---|---|
| 20 | 3.43 | 62.35 | 29.10 | 8.55 |
| 50 | 3.94 | 55.56 | 33.46 | 10.98 |

As can be seen above, lowering the temperature did exactly what conventional thinking dictates, merely lower the amount of products produced. Thus, the lower temperature alone does not cause the increase in cyclodextrin production.

EXAMPLE IV

This example further illustrates the criticality of the combination of cyclohexane with the lower temperature.

Two solutions were prepared and incubated in accordance with Example I at the temperatures listed in Table IV below using either cyclohexane or toluene. The amount of toluene was the same as the amount of cyclohexane.

TABLE IV

| Temp. (°C.) | Complexant | Total Amount (gr/100 ml) | Alpha (%) | Beta (%) | Gamma (%) |
|---|---|---|---|---|---|
| 20 | Cyclohexane | 11.69 | 39.8 | 60.2 | 0 |
| 20 | Toluene | 11.40 | 0 | 100 | 0 |
| 50 | Cyclohexane | 8.27 | 23 | 77 | 0 |
| 50 | Toluene | 12.90 | 0 | 100 | 0 |

As can be seen from the results, a lower temperature did not cause an increase in the amount of cyclodextrin produced when toluene was the complexant. In fact, the lower temperature caused a decrease in production of cyclodextrin.

It will be understood that the claims are intended to cover all changes and modifications of the preferred embodiments of the invention herein chosen for the purpose of illustration which do not constitute a departure from the spirit and scope of the invention.

What is claimed is:

1. In a process for making an alpha-cyclodextrin using a cyclomaltodextrin glucanotransferase obtained from *Bacillus macerans*, the improvement comprising treating a starch hydrolysate with said cyclomaltodextrin glucanotransferase obtained from *Bacillus macerans* at a temperature of between about 15° C. and about 40° C., the conversion being performed in the presence of cyclohexane and recovering said alpha-cyclodextrin.

2. The process of claim 1 wherein the amount of cyclohexane present is about 5 to about 10 percent of reaction volume.

3. The process of claim 1 wherein the starch hydrolysate has a DE between 1 and 10.

4. The process of claim 3 wherein the starch hydrolysate is a waxy starch hydrolysate.

5. A process for making alpha-cyclodextrin comprising the steps of:
   (a) treating an aqueous slurry of starch hydrolysate having a DE between 1 and 10 with cyclomaltodextrin glucanotransferase obtained from *Bacillus macerans*, at a temperature of between about 15° C. and about 40° C., the conversion being performed in the presence of cyclohexane, to form alpha-cyclodextrin without the formation of gamma-cyclodextrin;
   (b) recovering the alpha-cyclodextrin.

6. The process of claim 5 wherein the amount of cyclohexane present is about 5 to about 10 percent of reaction volume.

7. The process of claim 5 wherein the starch hydrolysate is a waxy starch hydrolysate.

8. The process of claim 5 wherein the treatment of the starch hydrolysate is for a time period of about 1 to 4 days.

9. The process of claim 5 wherein the amount of cyclohexane present is about 5% by volume of the slurry.

10. The process of claim 5 wherein the slurry has a solids content of about 30% to about 35% by weight.

* * * * *